US005484532A

United States Patent [19]
Rice

[11] Patent Number: 5,484,532
[45] Date of Patent: * Jan. 16, 1996

[54] RADIAL FLOW CHROMATOGRAPHY

[75] Inventor: Richard G. Rice, Baton Rouge, La.

[73] Assignee: Board of Supervisors of Louisiana State University and Agricultural and Mechanical College, Baton Rouge, La.

[*] Notice: The portion of the term of this patent subsequent to Jul. 18, 2012, has been disclaimed.

[21] Appl. No.: 454,534

[22] Filed: May 30, 1995

Related U.S. Application Data

[62] Division of Ser. No. 23,144, Feb. 24, 1993, Pat. No. 5,433,847, which is a continuation of Ser. No. 580,582, Sep. 11, 1990, which is a continuation-in-part of Ser. No. 430,495, Nov. 1, 1989, abandoned.

[51] Int. Cl.$^6$ ............................................. B01D 15/08
[52] U.S. Cl. ........................ 210/656; 210/658; 210/198.2
[58] Field of Search ................................. 210/656, 658, 210/659, 198.2, 255, 282, 489; 422/70; 436/162

[56] References Cited

U.S. PATENT DOCUMENTS

| | | | |
|---|---|---|---|
| 3,487,938 | 1/1970 | Patterson | 210/198.2 |
| 3,503,712 | 3/1970 | Sussman | 210/198.2 |
| 3,506,408 | 4/1970 | Kageyama | 210/284 |
| 3,763,879 | 10/1973 | Jaworek | 210/282 |
| 3,922,152 | 11/1975 | Kookoothakis | 210/284 |
| 4,154,583 | 5/1979 | Favre | 210/659 |
| 4,301,139 | 11/1981 | Feingers | 210/284 |
| 4,627,918 | 12/1986 | Saxena | 210/656 |
| 4,671,870 | 6/1987 | Tompa | 210/198.3 |
| 4,671,871 | 6/1987 | Szekely | 210/658 |
| 4,676,898 | 6/1987 | Saxena | 210/198.2 |
| 4,708,782 | 11/1987 | Andersen | 204/299 R |
| 4,726,822 | 2/1988 | Cates | 210/198.2 |

(List continued on next page.)

OTHER PUBLICATIONS

Rice, "Approximate Solutions for Batch, Packed Tube and Radial Flow Adsorbers—Comparison with Experiment," Chem. Eng. Sci., vol. 37, pp. 83–91 (1982).

Yee, "Fluid Mechanics and Transient Mass Transfer for Radial Flow in Pancake–shaped Packed Beds," M. S. Thesis, Louisiana State University, Baton Rouge, Louisiana (1987).

Saxena, et al., "Applications of Radial Flow Columns for Fast Affinity Chromatography," Am. Lab., pp. 112–120 (Oct. 1987).

Lapidus et al., "Mathematics of Adsorption in Beds. III," J. Phys. Chem. vol. 54, pp. 821–829 (1950).

Lapidus et al., "The Rate–Determining Steps in Radial Adsorption Analysis," J. Phys. Chem., vol. 56, pp. 373–383 (1952).

Hopf, "Radial Chromatography in Industry," Ind. & Eng. Chem., vol. 39, pp. 938–940 (1947).

Weil, "Indusrial Chromatography, Part 1–Column Chromatography and Radial Chromatography," Can. Chem. & Proc. Ind., pp. 956–959 (Nov. 1949).

Mitchell et al., "Preparation of Carotene Concentrates from Dehydrated Alfalfa Meal," Ind. & Eng. Chem., vol. 45, pp. 415–417 (1953).

Heftmann et al., "The Chromatofuge, An Apparatus for Preparative Rapid Radial Column Chromatography," J. Chromatogr., vol. 66, pp. 365–369 (1972).

Borie, "Design, Construction and Experiments on a Radial Flow Liquid Chromatograph," M. S. Thesis, Louisiana State University, Baton Rogue, Louisiana (1989).

Rice et al., "Radial Flow Chromatography in Compressed Pancake–Shaped Beds," Preprint, to be published in Chem Eng. Comm., 1990.

Primary Examiner—Ernest G. Therkorn
Attorney, Agent, or Firm—John H. Runnels

[57] ABSTRACT

A radial flow chromatograph in which the bed is tightly compressed, or a chromatographic series comprised of a series of several such beds. A process for separating species in a fluid by driving the fluid radially through one or more tightly compressed beds.

7 Claims, 9 Drawing Sheets

U.S. PATENT DOCUMENTS

| | | | | |
|---|---|---|---|---|
| 4,740,298 | 4/1988 | Andersen | | 210/198.3 |
| 4,749,481 | 6/1988 | Wheatley | | 210/282 |
| 4,816,159 | 3/1989 | Khosah | | 210/659 |
| 4,840,730 | 6/1989 | Saxena | | 210/198.2 |
| 4,865,729 | 9/1989 | Saxena | | 210/198.2 |
| 4,891,133 | 1/1990 | Colvin | | 210/198.2 |
| 5,433,847 | 7/1995 | Rice | | 210/198.2 |

COMPARISON OF EQUILIBRIUM MODEL WITH EXPERMENT

COMPARISON OF EQUILIBRIUM MODEL WITH EXPERIMENT

IMPACT OF BED POROSITY ON IMPULSE RESPONSE
(He FLOW = 100 CC/MIN)

IMPACT OF CARRIER GAS FLOW ON IMPULSE RESPONSE (BED POROSITY = 0.20)

RADIAL FLOW CHROMATOGRAPHY

STATEMENT REGARDING FEDERALLY SPONSORED RESEARCH

This invention was made with Government support under grant CBT-8804705 awarded by the National Science Foundation. The Government has certain rights in this invention.

RELATED APPLICATION

This application is a division of application Ser. No. 08/023,144, filed Feb. 24, 1993, now U.S. Pat. No. 5,433,847, which is a continuation of application Ser. No. 07/580,582, now abandoned, filed Sep. 11, 1990, which is a continuation-in-part of application Ser. No. 07/430,495, filed Nov. 1, 1989, now abandoned.

BACKGROUND OF THE INVENTION

This invention pertains to chromatography, specifically to radial flow chromatography, in which the flow is essentially in a radial direction in the sorbent bed, rather than in an axial direction.

Radial chromatography dates back at least to 1947 when Hopf, P., Ind. Eng. Chem., Vol.39, p. 938 (1947), invented the so-called chromatofuge for separating liquid solutes using centrifugal force. This device and its successors, such as Well, H., Canadian Chem. and Process Ind., November (1949); Mitchell, H. L., Schrenk, W. G., and Silker, R. E., Ind. and Eng. Chem., vol. 45, p. 415 (1953), were physically large and cumbersome, and were used primarily for preparative-scale separations. Heftmann, E., Krochta, J. M., and Farkas, D. F., J. Chrom., vol, 66, p. 365 (1972), reduced the size of the liquid separator, and also increased rotational speed to 1950 revolutions per minute.

The radial flow configuration for packed beds of particles is a recent enhancement procedure which has been used in chemical reactors, and which has been suggested generally as a possible mode for analytical chromatography. Rice, R. G., Chem. Eng. Sci., vol. 37, p. 83 (1982).

Liquid radial flow chromatography driven by a pressure drop across the separation medium has been discussed in references such as Saxena, U.S. Pat No. 4,627,918. Liquid radial flow in a thin separation medium similar to separation media used in thin layer chromatography has been discussed in references such as Andresen and Saxena, U.S. Pat. No. 4,708,782.

Yee, M., M. S. Thesis, Louisiana State University, Baton Rouge La. (1987), attempted gas radial flow chromatography, wherein pressure was used to drive gas through the chromatographic bed. Yee compressed the beds used, but was unable to achieve uniform radial flow. Uneven distribution of the fluid flow through the bed was a serious problem in Yee's results. Unless the radial flow of fluid can be made uniform, the technique's usefulness for separations, particularly analytical separations, is severely limited.

SUMMARY OF THE INVENTION

Radial flow chromatography can give rapid results. Band-broadening and uneven distribution of the radial flow can be significantly reduced by tightly compressing the packed sorbent bed. Compression of the bed serves two purposes: it promotes a uniform bed, which in turn promoters uniform radial flow; and it reduces bed voidage, which minimizes inter-particle hold-up. Such a tightly and uniformly packed, "pancake-shaped" bed can have substantially uniform radial flow, and can exhibit chromatographic flow behavior equivalent to a much larger, axial-flow, packed sorbent bed. In addition to a reduction in size, the pressure drop needed for radial flow chromatography may be orders of magnitude lower than the pressure drop for comparable flow rates in an axial-flow packed tube. The fluid used is not limited to a single type of phase such as a liquid, but may be a liquid, a gas, or a supercritical fluid. Easily replaceable, pre-manufactured radial flow sorbent diskettes may be used in single-pass or multiple-pass chromatographs. Other features and advantages of the invention will be apparent from the following description of the invention, and from the claims.

DETAILED DESCRIPTION OF THE INVENTION

Figure 1:
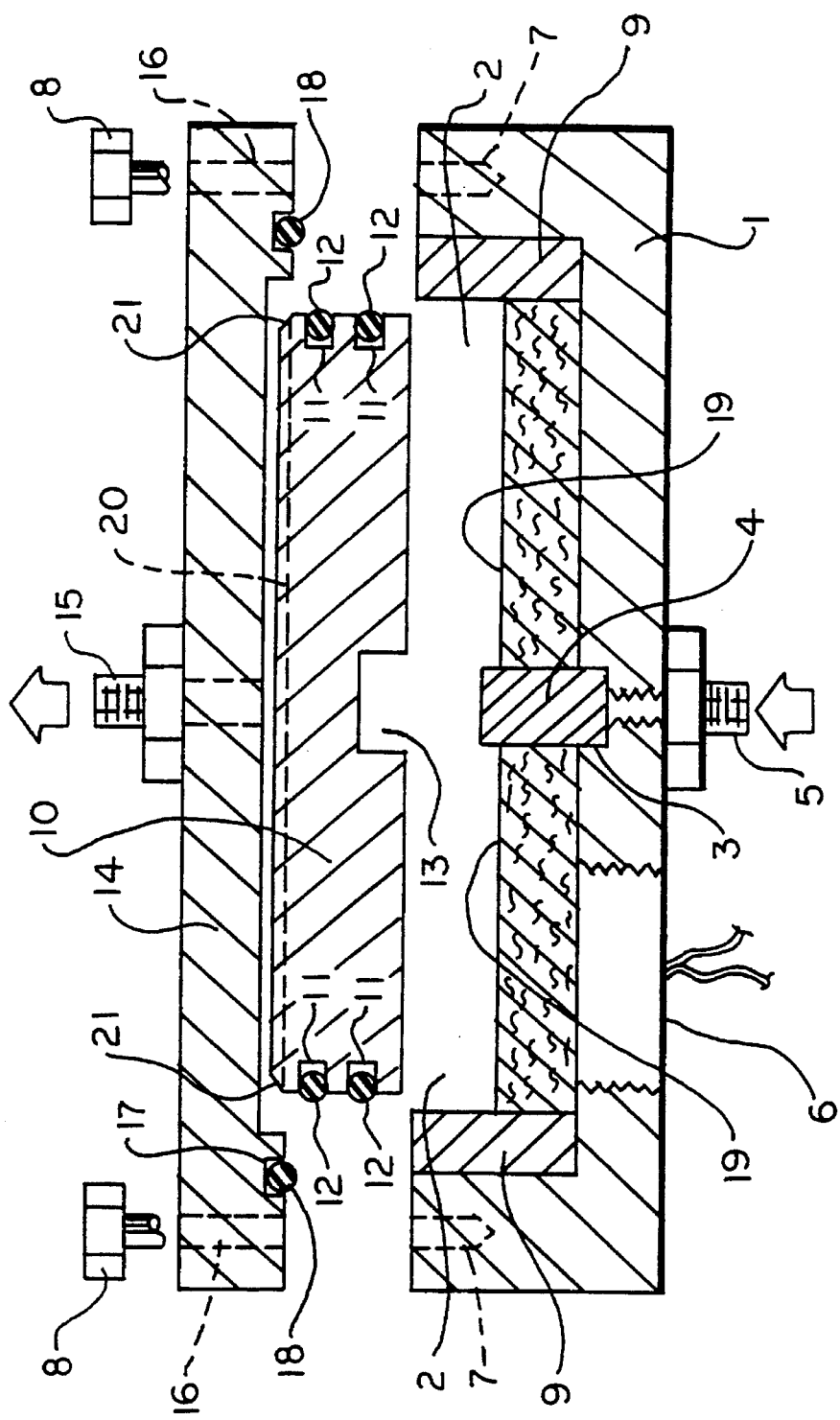
FIG. 1 illustrates the MARK II RFC chromatograph.

An embodiment of the present invention was built, the MARK II RFC chromatograph, illustrated in FIG. 1. Receiver 1, approximately 4.5 inch (11.4 cm) wide and 1.6 inch (4.1 cm) high, machined from 416 stainless steel, had a right-circular-cylindrical depression 2 approximately 3 inch (7.6 cm) in diameter and 0.875inch (2.2 cm) high, a depression 3 for holding a porous inner septum a, and a passage 5 for inlet fluid to pass into porous inner septum 4. Porous inner septum 4, outer diameter 0.25 inch (0.64 cm), inner diameter 0.125 inch (0.32 cm), pore size 2 micron, was made of sintered steel, and was manufactured by Mott Metallurgical Corporation of Farmington, Conn.: Mott Porous 316L Stainless steel series no. 1400, catalog number 1400-0.250-0-0.125-6-2. A pressure transducer 6 was imbedded in receiver 1 to measure the pressure within depression 2 of receiver 1. Receiver 1 had threaded bores 7 for receiving bolts 8. Along the outer wall of depression 2 was annular porous septum 9, made of sintered bronze, outer diameter 3 inch (7.62 cm), inner diameter 2.875 inch (7.32 cm), pore size 20 micron, manufactured by Thermet, Inc. of Glouchester, Mass., model no. 103A. Sintered steel would also be a good material to use for annular porous septum 9. Both porous inner septum 4 and annular porous septum 9 were manufactured through standard metallurgical sintering processes. A right-circular-cylindrical plunger 10, machined from 416 stainless steel, had a diameter slightly smaller than the inner diameter of annular porous septum 9, grooves 11 for receiving O-rings 12, a depression 13 for receiving porous inner septum 4, and eight uniformly spaced, 1/16 inch (0.16 cm) wide and 1/16 inch (0.16 cm) deep rectangular grooves 20 leading from a bevel header 21, 1/16 inch (0.16 cm) deep and 0.1083 inch (0.275 cm) long, around the circumference of plunger 10. Plunger 10, together with O-rings 12, formed a pressure-tight seal against annular porous septum 9 and cap 14 when force was applied to plunger 10 in the direction towards receiver 1. Cap 14, machined from 416 stainless steel, fitted over and in contact with plunger 10 and on top of and in contact with receiver 1 and annular porous septum 9. Cap 14 had a passage 15 for outlet fluid, threaded bores 16 aligned with threaded bores 7 for receiving bolts 8, and grooves 17 for receiving O-ring 18. O-ring 18 rested on top of both receiver 1 and annular porous septum 9, and formed a pressure-tight seal between cap 14 and receiver 1 and annular porous septum 9 when force was applied to cap 14 in the direction towards receiver 1.

Sorbent bed 19, sieved 120–140 mesh (U.S. Standard Sieve) particles of Alcoa grade gamma-phase alumina, was placed in depression 2 as a slurry in hexane. The solvent was evaporated under heat and vacuum to form an initial bed. The dimensions of the annular bed were: inner radius, 0.3175 cm; outer radius, 3.65 cm. Plunger 10 was placed on the bed, and cap 14 was placed over plunger 10 and receiver 1. Bolts 8 were threaded through bores 16 and 7, and bolts 8 were tightened until pressure transducer 6 indicated a pressure of 5000 pounds per square inch ($3.45 \times 10^7$ pascal). The height of the bed was then determined to be 0.476 cm. The chromatograph was then placed in a standard chromatograph oven (Bendix Model 2200), and connected to conventional injector and detector ports via fine capillary tubing.

Helium was passed through inlet 5 to porous inner septum 4, from which it flowed radially outward through sorbent bed 19, passed through annular porous septum 9, was collected in bevel header 21, and then passed through grooves 20 to outlet 15, and then to a conventional thermal conductivity detector. The bed was conditioned for several days by this helium passage, with the entire chromatograph maintained at a temperature of 100° C.

The dynamic porosity (voidage) of the bed was determined by first measuring flow versus pressure drop for an empty bed, and then taking the same measurements for a packed bed. By comparing the former to the latter, bed porosity was estimated to be 12%. The porosity was estimated by the methods of Yee, M., M. S. Thesis, Louisiana State University, Baton Rouge, La. (1987), which is incorporated by reference, with particular note to pp. 24–41 and equation 2.4–4 on p. 38. This 12% figure should be compared to the typical 35–40% porosity of traditional axial-flow chromatographic columns. Measurements of pressure drop through the bed versus flow rate indicated that laminar flow conditions prevailed.

Response experiments (illustrated in FIGS. 2 and 3) were conducted by injecting a pulse of methane into flowing helium gas. The elution profile was recorded versus time for several carrier gas flow rates. Oven temperature was maintained at 100° C. for all tests.

Figure 2:
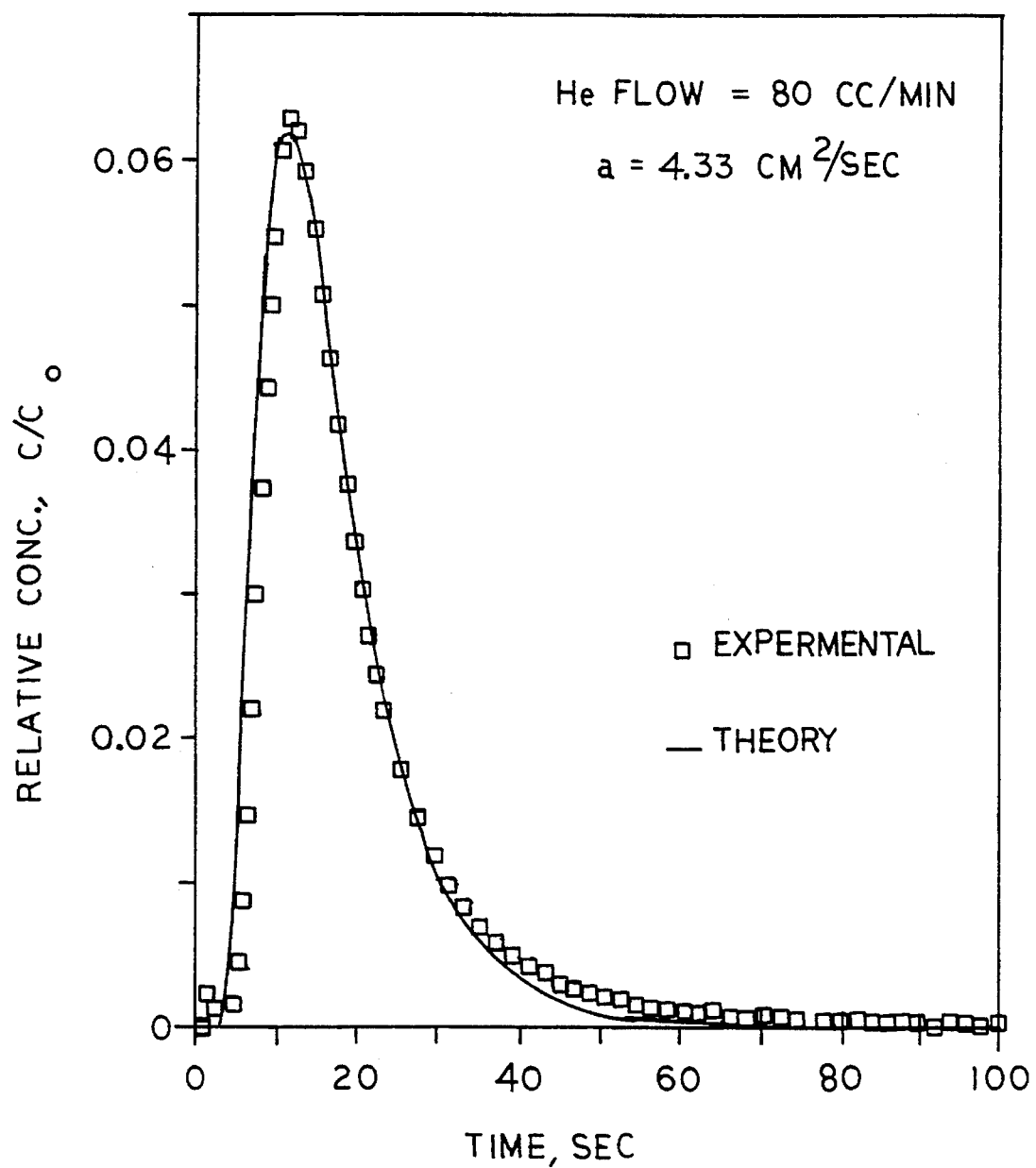
FIGS. 2 and 3 illustrate typical response curves for the MARK II RFC.
Figure 3:
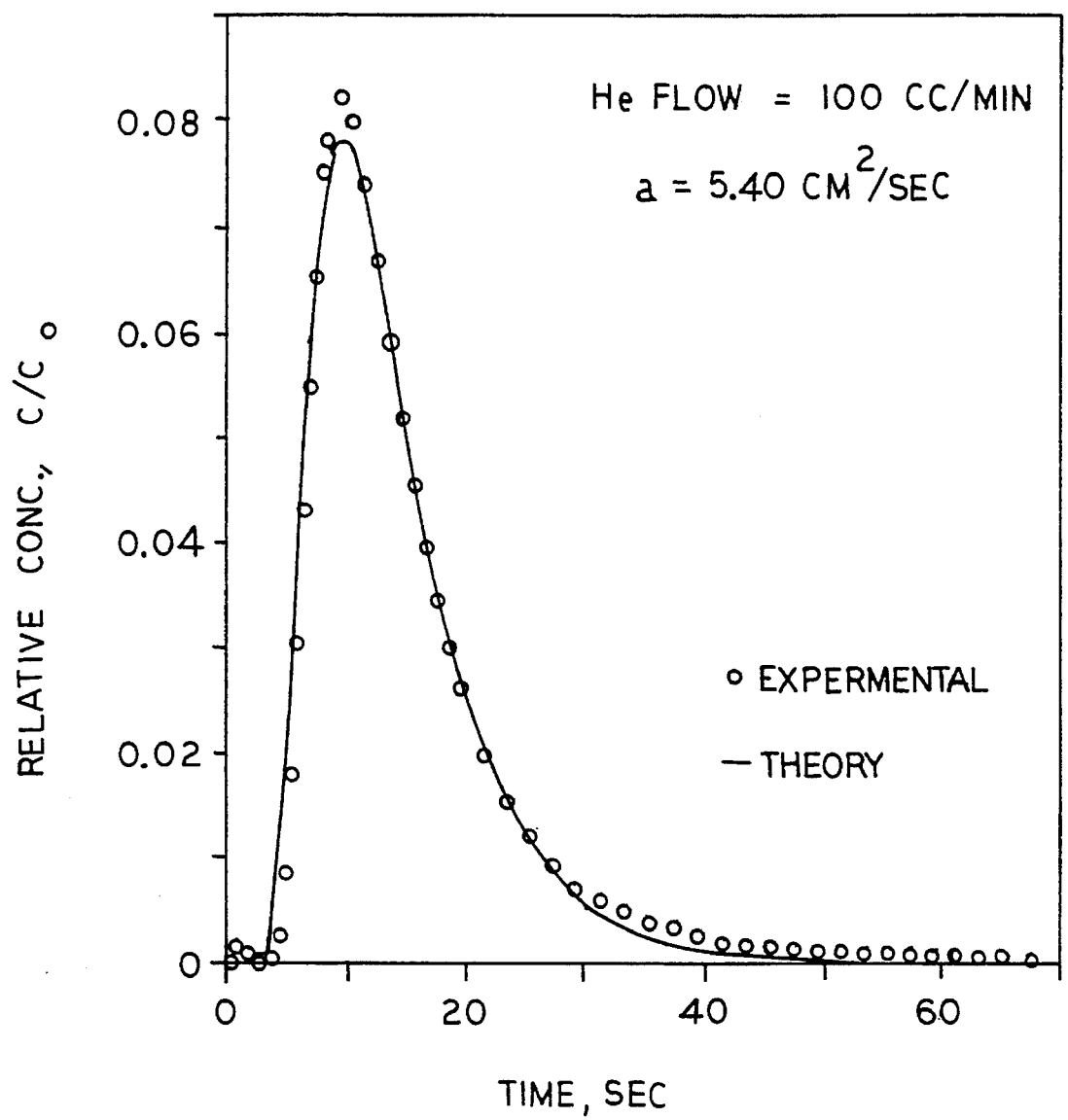

FIGS. 2 and 3 illustrate typical response curves for the MARK II RFC. Tailing arose from dispersion in the flow direction, which is believed to be due primarily to molecular diffusion. The behavior is non-Gaussian, due to the unique physical interaction of diffusion and convection in radial flow.

TABLE I

| | SUMMARY OF EXPERIMENTAL RESULTS | | | |
|---|---|---|---|---|
| TRIAL | CARRIER GAS FLOWRATE (cc/min) | K | DISPERSION COEFFICIENT (cm$^2$/sec) | IAE (%) |
| A | 100 | 1.38 | 0.88 | 10.2 |
| B | 100 | 1.38 | 0.92 | 8.9 |
| C | 80 | 1.65 | 1.31 | 14.8 |
| D | 80 | 1.40 | 0.96 | 11.4 |
| E | 60 | 1.57 | 1.00 | 12.6 |
| F | 60 | 1.46 | 0.88 | 10.3 |

In Table I, "IAE" refers to the integral absolute error in comparing experiment to theory; and "K" is the linear partition coefficient.

Figure 4:
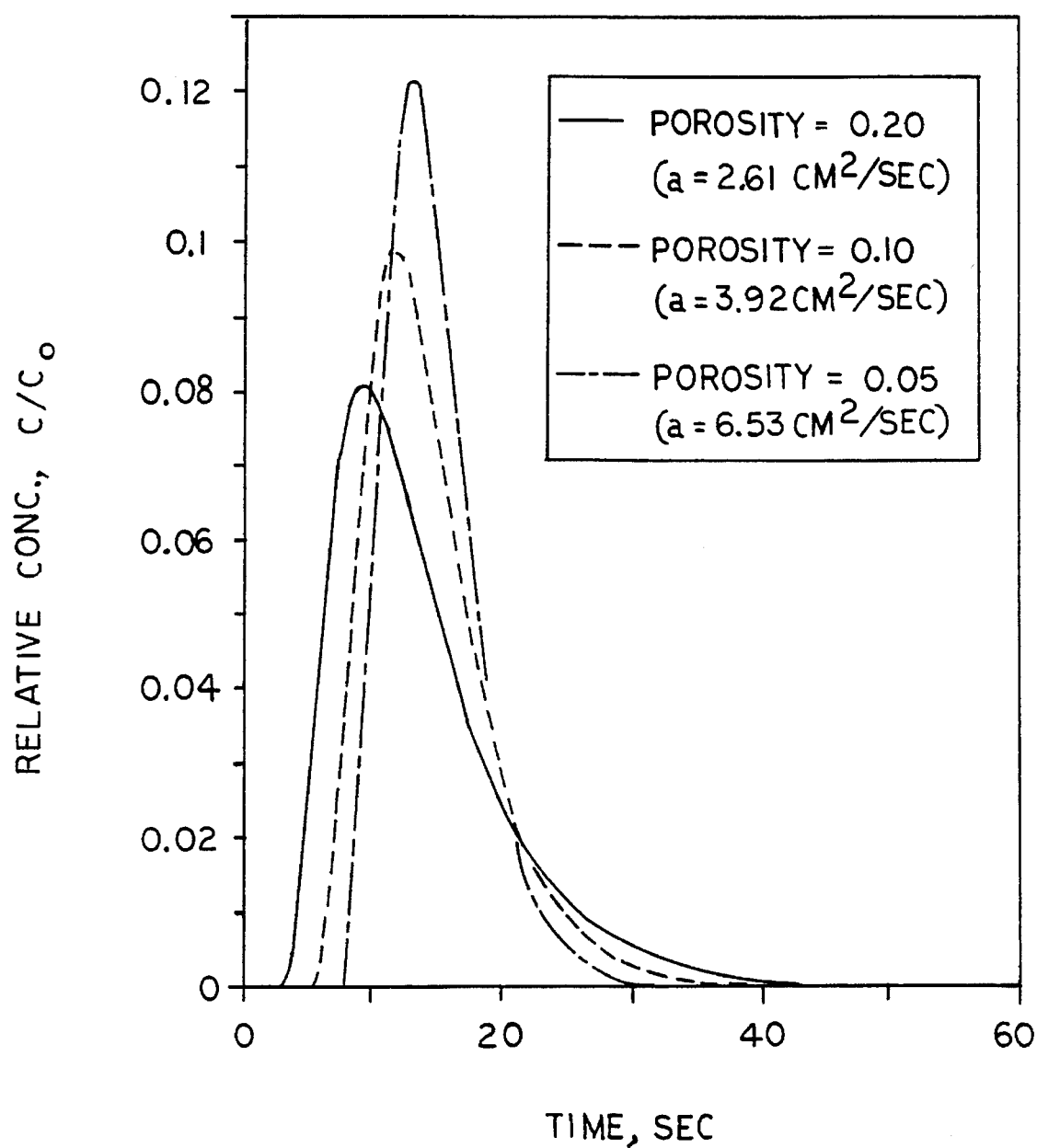
FIG. 4 illustrates a computer simulation of the effect of bed porosity on peak width.
Figure 5:
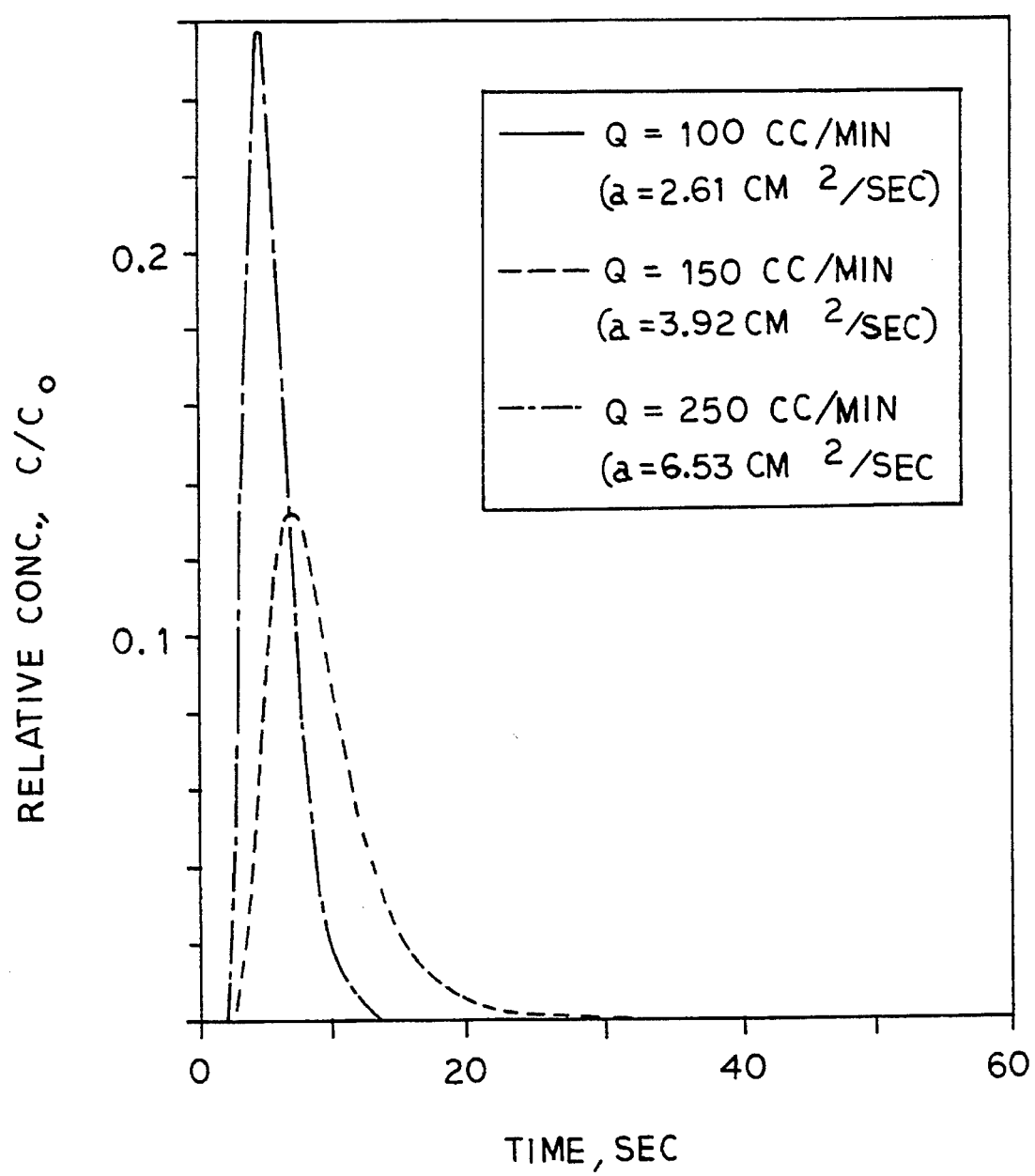
FIG. 5 illustrates a computer simulation of the effect of carrier gas flow rate on peak width.

Three ways to sharpen peaks and to minimize tailing are (1) to increase the flow rate, (2) to reduce the bed thickness, and (3) to increase compression. Illustrations of reducing the width of the peaks by increasing compression and by increasing flow rate are shown in FIGS. 4 and 5, respectively, which illustrate computer simulations. These simulations show that an optimum combination of high compression and increased flow will give satisfactory peak configurations.

It is believed that under conditions typical for radial flow chromatography, mixing due to molecular diffusion in the flow direction was the controlling step in producing band broadening and tailing. these phenomena occur mainly because convection and diffusion are of the same order of magnitude. These phenomena can be controlled by strategies including: (i) increased bed compression, (ii) increased convection via increasing flow, decreasing bed thickness, and decreasing bed voidage, (iii) multiple passes to enhance the number of effective separation stages, and (iv) smaller particle sizes. Option (iii), multiple passes, may involve successive stages in which (1) all flow is in the same direction, or (2) is alternately radially outward and then radially inward, or (3) is alternately radially inward and then radially outward. (Flow which is radially inward may be said to be in a "radially opposite direction" from flow which is radially outward.)

On theoretical grounds, the following predictions for radial flow chromatography are made. Peak sharpening should increase as convection increases; or as diffusivity decreases. The system time constant should increase as the radius of the bed increases; or as porosity decreases; or as diffusivity decreases; or as the adsorption coefficient decreases. In fact, as the porosity becomes small (but before compression sufficient to cause "welding" of the particles to one another, the time constant increase dramatically; thus a relatively small radial-flow bed can exhibit behavior similar to that of a much larger, axial-flow tube. Also note that the time constant increases as diffusivity decreases, which is not true for conventional axial-flow chromatography. Separations by "kinetic" mechanisms, in addition to the more usual partition-type mechanisms, are possible. It is possible that without compression, but with additional grinding of an adsorbent—perhaps to about 400 mesh—results would be similar to those achieved by compression of the bed.

Because the pressure drops required in radial flow chromatography are low, particle sizes can be much smaller than those used in axial flow chromatography. The effects of intraparticle resistance can thus be virtually eliminated. Moreover, because direct-contact heating can be applied (for example via the plunger), temperature programming can be made quite rapid, and bulky convection ovens can be eliminated, leading to very fast, compact units for analytical work. Low pressure drops can eliminate dangers associated with high pressure chromatography, especially if the user uses pre-manufactured chromatographic diskettes as discussed below.

Compression of the bed must be optimized, for too much compression reduces a bed's sensitivity to different species, and can eventually cause particles to weld together. It is important to minimize inlet and outlet volumes as much as possible to reduce tailing. For example, in the MARK III RFC embodiment discussed below, compared to the MARK II RFC embodiment discussed above, bevel header 21 was eliminated to reduce total outlet volume. For the same reason, the size of the outlet grooves was greatly reduced.

Figure 6:
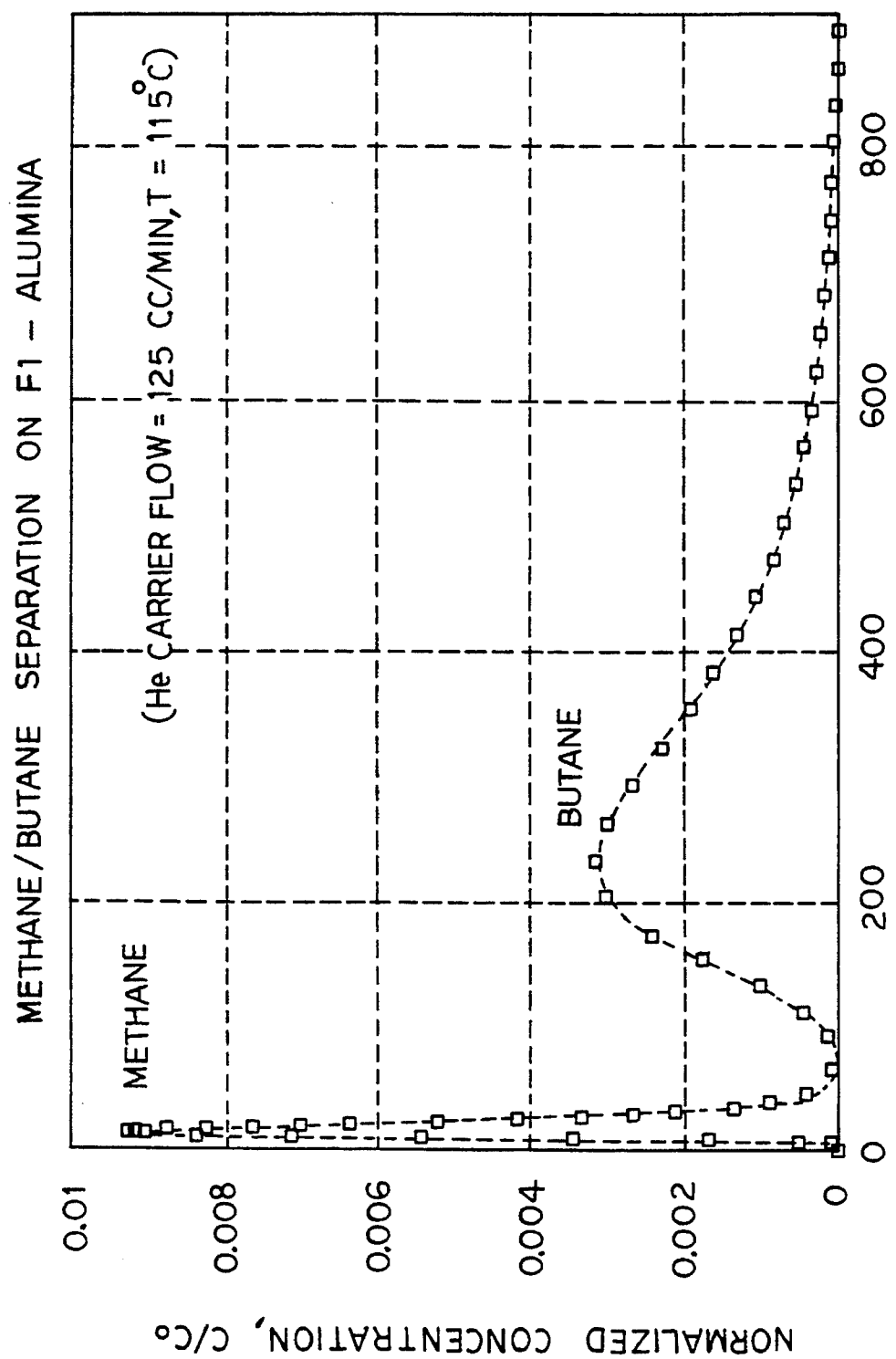
FIG. 6 illustrates a separation of methane and butane in the MARK III RFC.

FIG. 6 illustrates the results of a separation achieved on F-1 alumina in the MARK III RFC. (The MARK III RFC chromatograph is discussed below). A pulse comprising a 1:3 mixture by volume of methane and butane was injected into a carrier of flowing helium gas. The helium flow rate was 125 cc/min, and the oven temperature was maintained at 115° C. The points in FIG. 6 correspond to the experimental data, and the dashed lines correspond to a theoretical, computer-generated response curve. The first peak in FIG. 6 corresponds to methane, and the second peak to butane. IAE for methane was 6.17%, and IAE for butane was 1.46%. The Peclet number was 4.05 for methane, and 3.75 for butane. The time constant was 315.39 sec for methane, and 4720.38 sec for butane. Sharper, and better separated peaks would probably be obtained by running at a higher temperature, or by using temperature programming.

Figure 7:
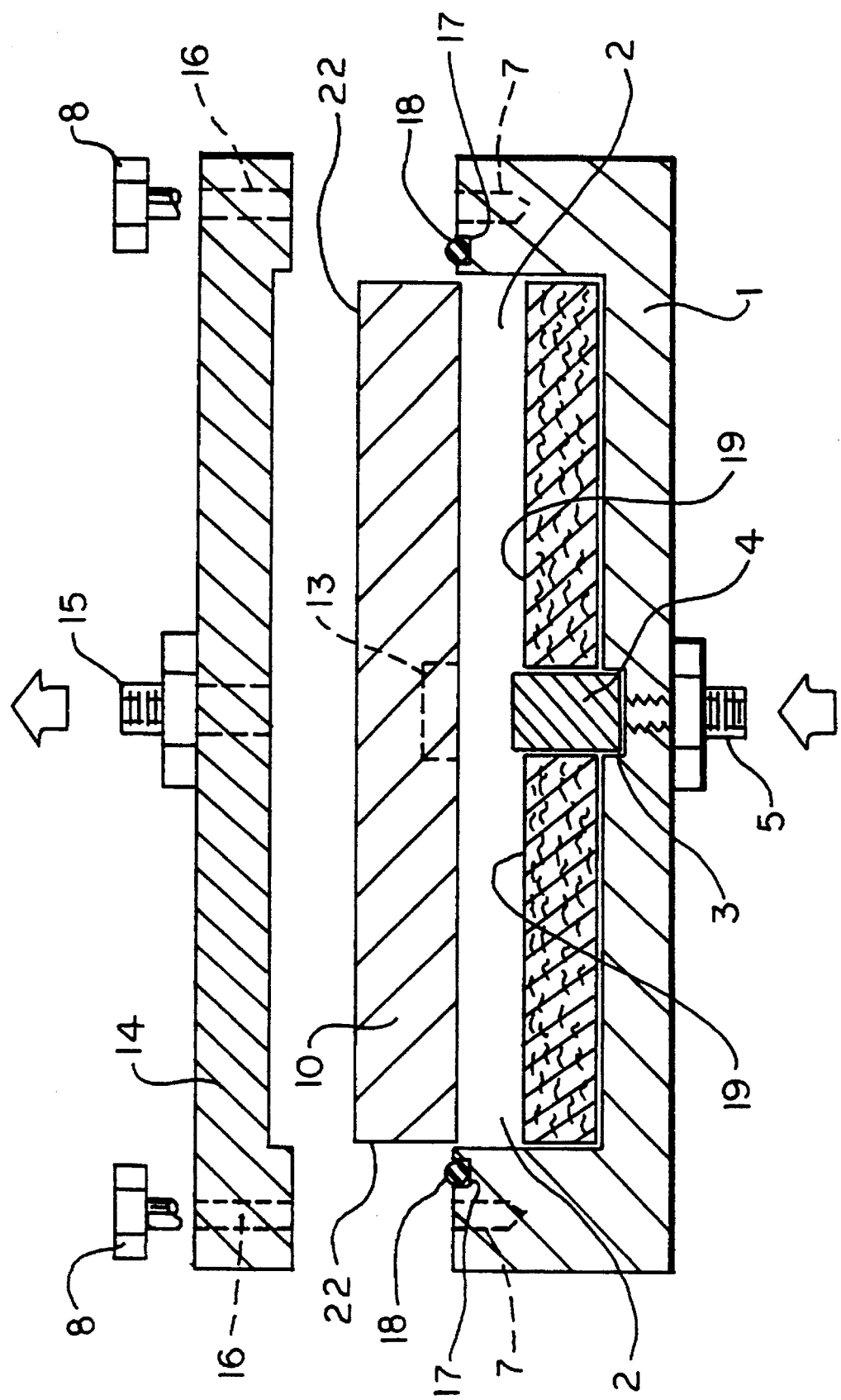
FIG. 7 illustrates the MARK III RFC chromatograph.

An improved embodiment of the radial flow chromatograph of the present invention, the MARK III RFC, was constructed, and is illustrated in FIG. 7. Its construction was similar to that of the MARK II RFC, and the same reference numerals correspond to the same or analogous parts in both chromatographs, except as noted otherwise. In the MARK III RFC of FIG. 7, compared to the MARK II RFC of FIG. 1, the following principal changes were made: Annular porous septum 9 was eliminated, so that plunger 10 and sorbent bed 19 were adjacent the sides of receiver 1 and cap 14. Sorbent bed 19 was made from 100–120 mesh F-1 alumina. Grooves 11 and O-rings 12 were eliminated. Pressure transducer 6 was removed. Bevel header 21 was eliminated. Grooves 20 were replaced by twenty-six evenly spaced grooves 22. Each groove 22 (not shown) was V-shaped, having a 0.006 inch (150 micron) base and a 0.006 inch (150 micron) depth, and traversed both the side of plunger 10, and a radius of plunger 10 from the side to the center of plunger 10. Thus the MARK [II RFC was generally similar to the MARK II RFC, with the total outlet volume reduced. The oven used was Hewlett-Packard Model 5890. Another difference between the two embodiments was that in the MARK II RFC, the bed was compressed by tightening bolts 8 until the compression reached 5000 pounds per square inch ($3.45 \times 10^7$ pascal). In the MARK III RFC, the bed was compressed by placing the chromatograph in a hydraulic press, and compressing to 10,000 pounds per square inch ($6.9 \times 10^7$ pascal). The chromatograph was then removed from the press, and then bolts 8 were quickly tightened. The latter approach has the advantages that higher pressures and therefore compressions were generally possible, and that outward bowing of cap 14 was virtually eliminated. The grooves 22 could be replaced by an annular, sintered ring of alumina around plunger 10.

It is advantageous to prepare the sorbent bed by first wet-packing the sorbent as a slurry in a volatile liquid having a low surface tension, and then driving the liquid off. This technique helps reduce gaps or dead volume within the bed. It is preferable to use a liquid having a low surface tension, to help reduce bubbles within the bed. To help evaporate the liquid substantially completely, applying heat, vacuum, or both will typically be useful. The liquid may be driven off before or during compression; the latter in more uniform The chromatograph of the present invention may be used in gas, liquid, or supercritical fluid chromatography. It is particularly suited for applications in liquid and supercritical fluid chromatography because diffusivity is so small, and because some embodiments of the chromatograph of the present invention, such as the previously constructed MARK II and MARK III RFC's, may be designed for the high pressures needed for supercritical fluids, particularly where the chromatograph already possesses high pressure capability because it has been designed for in situ compression of the sorbent bed.

Adsorbents used for any fluid should have a mean particle diameter less than 300 micron, preferably less than about 100 micron, and most preferably less than about 10 micron. This mean particle diameter should be less than about 0.05 times the height of the cylinder (i.e., the dimension of the cylinder in the axial direction. Within these limits, a thinner bed (i.e., one with a smaller height) should generally have a performance superior to that of a thicker bed. Suitable adsorbents for liquid chromatography are well known, such as 3-micron silica and 5-micron silica. Any solid sorbent used for gas chromatography may also be used in supercritical fluid chromatography, provided that no part of the sorbent or any coating on the sorbent is dissolved by the supercritical fluid. Examples of suitable sorbents for gas or supercritical fluid chromatography include active carbon (e.g., graphite, carbosieve), active alumina, silica gel, and certain porous polymers (such as Poropak Q, Poropak R, Poropak P, and Durapak).

The porosity of the packed bed should be less than 30%; a lower limit on porosity occurs where the particles begin to weld to one another. The porosity is preferably between about 8% and about 12%. Within practical limits, the finer the particles, and the greater the compression, the better the separation should be.

While the MARK II and MARK III RFC embodiments of the present invention used in situ compression of the bed, a feature which makes the chromatograph particularly suited for use with the pressures typically required for supercritical fluids, the invention would also work without in situ compression, with a uniform bed which had previously been prepared with sufficiently small particle size and sufficiently low porosity.

Such beds may be manufactured in advance in such a way that they could be easily stored, inserted, and removed in a radial flow chromatograph by the user. Such a pre-manufactured bed may comprise one or more layers of sorbent within a circular, diskette-shaped container. In a preferred embodiment, illustrated in cross-section in the top portion of FIG. 8, the diskette comprises circular confining plates 25 and 26, plate 26 having O-ring 27 in a groove around the periphery. Between plates 25 and 26 are pre-compressed sorbent beds 28 and 29. Sorbent beds 28 and 29 are separated from one another by circular separating plate 30, plate 30 having a number of microgrooves positioned around its periphery and parallel to its axis. Between each pair of adjacent surfaces of a plate 25, 26, or 30, and a sorbent bed 28 or 29 is a thin Teflon or other suitable polymeric layer 31 adhering to the surface of the plate. Plate 25 has a centrally located inlet nozzle 32, and plate 26 has a centrally located exit hole 33. In use, fluid flows in through inlet nozzle 32, radially outward through sorbent bed 28, through the peripheral microgrooves of plate radially inward through sorbent bed 29, and out through outlet hole 33.

Figure 8:
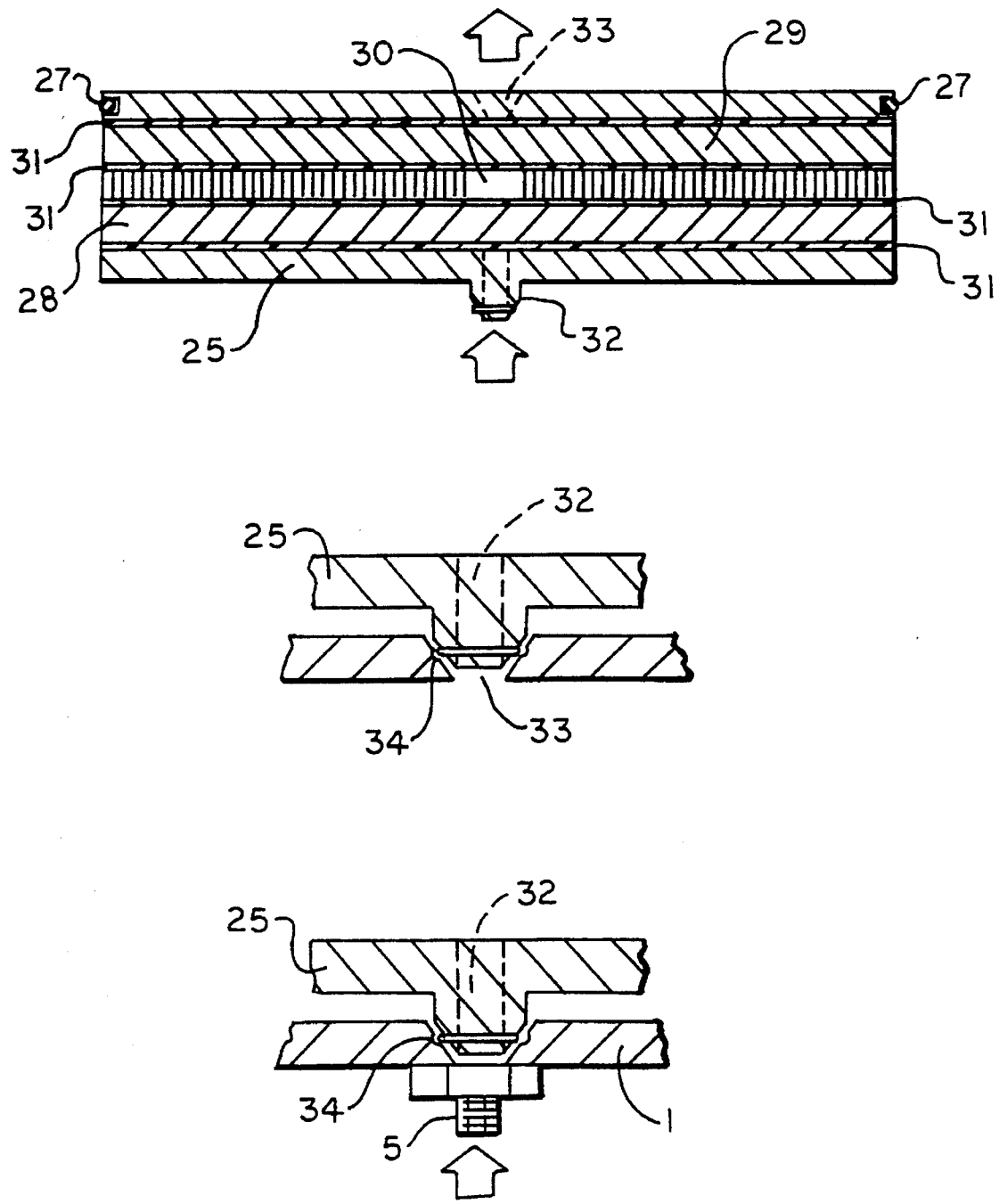
FIG. 8 illustrates a cross section of a replaceable, diskette-type chromatograph bed suitable for use in a radial flow chromatograph.

The middle portion of FIG. 8 illustrates one way in which adjacent diskettes may be joined to one another. Nozzle 32 of the top diskette has a fitted O-ring which snaps into a corresponding groove 34 in exit hole 33 of the bottom diskette. The bottom portion of FIG. 8 illustrates an analogous manner for joining a diskette to receiver 1 of the chromatograph. Although not illustrated, an analogous manner for joining a diskette to cap 14 of the chromatograph could also be used.

Nozzle 32 in FIG. 8 is not shown to scale, for clarity of illustration. But in a preferred embodiment, the relative sizes and shapes of nozzle 32 and its O-ring, of exit hole 33, and of groove 34, are such that the joint is flush—i.e., such that adjacent joined faces touch one another, or are in very close proximity to one another.

The sorbent beds may be pre-compressed, and then assembled with the other components of the diskette; or the components may be assembled uncompressed and then subjected to pressure to form the finished diskette. The latter alternative has the advantage of promoting bonding between the sorbent beds and the Teflon or other polymeric layer. In either case, substantial uniformity in applying the pressure is necessary to produce a quality bed. Such a diskette could be prepared in the MARK II or MARK III RFC, or could be separately produced, or could be mass-produced. The layer of Teflon or other suitable polymeric material 31 functions to allow uniform adhesion of plates 25, 26, and 30 to beds 28 and 29 without leaving dead space between the beds and the plates. This material should be able to withstand the combination of temperature and fluid conditions which will be used in the chromatographic separation without significant softening, disintegration, or dissolution, and without otherwise having a significant adverse effect on chromatographic separations. The diskette holds itself together through bonding of the Teflon or other polymer both to the beds and to the plates; and by the internal cohesion of the consolidated beds, which have a consistency roughly similar to that of concrete. The confining plates 25 and 26 and separating plate 30 may be constructed of any material of sufficiently high strength, thickness, heat conductivity, and inertness to conditions typically encountered during chromatographic use; such materials include, for example, aluminum, stainless steel, high conductivity polymer composites, etc. Inlet 32 and exit 33 should be located adjacent the center of the sorbent beds, and should have small fluid passages, preferably less than about 4 mm in diameter. The peripheral microgrooves in plate 30 should preferably be small in size (i.e., have a depth less than about the average particle diameter, whether or not the replaceable diskette embodiment is used), and should be spaced uniformly around the edge of the plate. Although the preferred diskette embodiment illustrated in FIG. 8 has two sorbent beds, it is also possible to make diskettes containing a greater number of beds, or with only a single bed. In the latter case, or more generally with an odd number of beds in a diskette, if the inflow is at the center of the first bed, suitable provision would have to be made for collecting the outflow at the periphery of the last bed, or vice versa. See, e.g., the single-bed MARK II RFC discussed above.

Figure 9:
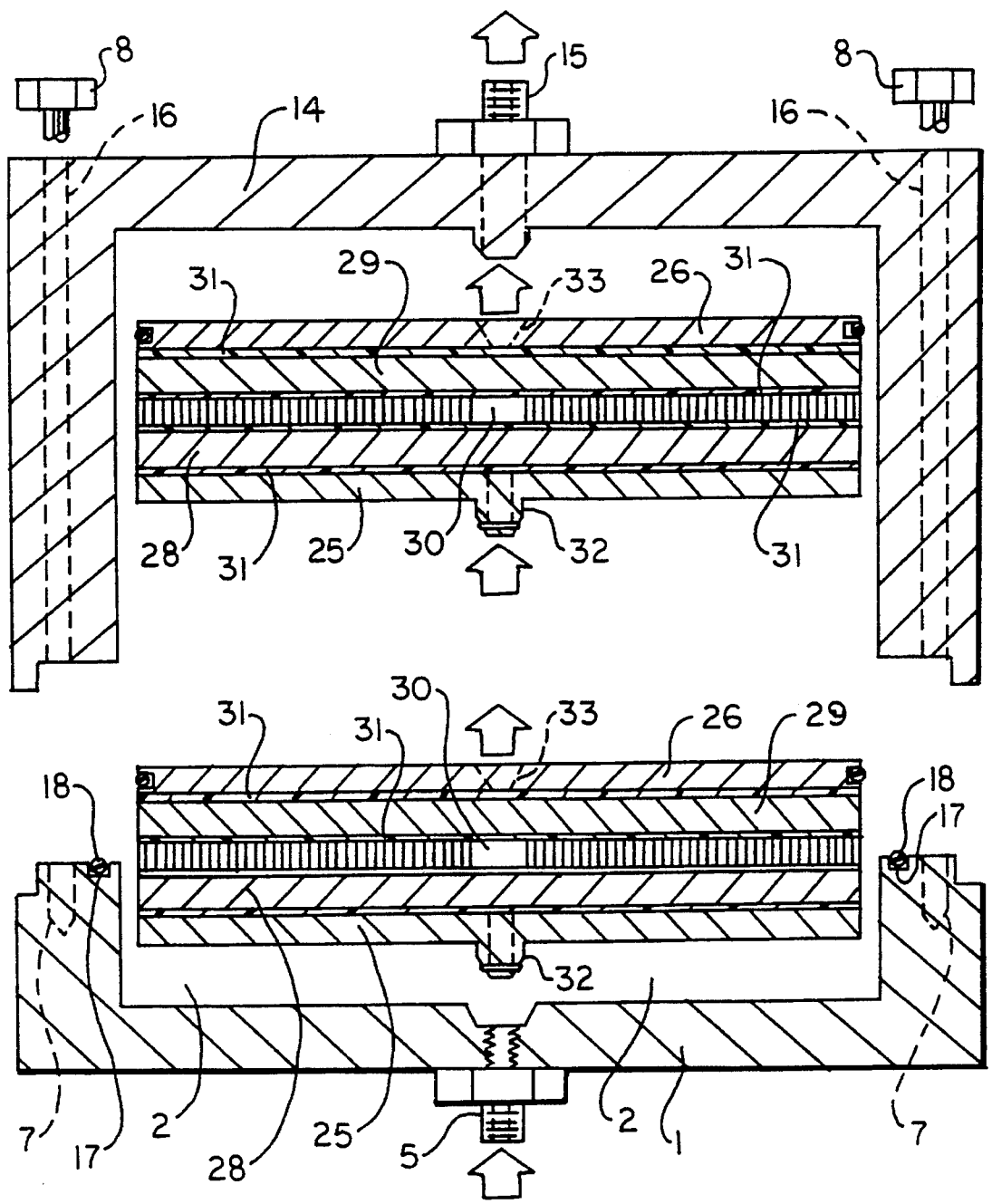
FIG. 9 illustrates radial flow chromatograph equipped with multiple diskettes for multiple-pass chromatography.

A single such disposable diskette can be used in an RFC, or multiple diskettes can be used in a single RFC. FIG. 9 illustrates an embodiment containing multiple such diskettes in a single RFC chamber. O-rings 27 help prevent undesirable "short-circuiting" of fluid flow. The individual sorbent beds within the diskettes preferably have a thickness between about 0.5 mm and about 2 mm. The number of diskettes used depends on the degree of separation desired, or on the type of separation desired.

The diskette embodiments illustrated in FIGS. 8 and 9 use O-ring 27 as a seal to prevent "short-circuiting" of fluid flow. An alternative sealing means, not illustrated, is the following. O-ring 27 and its associated groove are eliminated. A circular band (such as a steel band) whose inner diameter is barely larger than the outer diameter of the diskette, and whose height is the same as the height of the diskette or a little higher, is placed around the diskette. The band is then welded or crimped to plates 25 and 26 in such a way that no substantial fluid flow past plates 25 or 26 will occur, but such that flow may still occur through the microgrooves of plate 30. Thus the user of a premanufactured diskette will see only its cylindrical exterior, with a nozzle on one side, and a hole adapted to receive a nozzle on the other side.

The diskettes used in a multiple-pass chamber need not be identical. For example, a first diskette for a coarse separation could be followed by a second diskette for a finer separation. As an additional example, it might be desirable to separate a mixture of three species A, B, and C; where no conveniently available separation medium will separate all three species from one another; but where medium 1 will separate A and B on the one hand, from C on the other hand; and where medium 2 will separate A and C on the one hand, from B on the other hand. Then A, B, and C could all be separated from one another by using a radial flow chromatograph having two diskettes in series: one packed with medium 1, and one packed with medium 2. Two such chromatographic beds may be said to be "not substantially similar" if their chromatographic separation characteristics are different in any substantial way. Differences between chromatographic beds which will frequently cause the beds to be "not substantially similar" include different particle sizes, different porosities, different voidages, different compressions of the beds, different compositions of the beds, and different sizes of the beds. It would also be possible to have multiple beds not substantially identical to one another partitioned within a single diskette.

I claim:

1. A process for separating at least two different species in a fluid, said process comprising the steps of:
   (a) introducing the fluid containing the species into a bed, wherein the bed:
      (i) has the shape of a right circular cylinder;
      (ii) is comprised of sorbent particles, wherein the mean diameter of said particles is less than 300 micron, and wherein the distribution of said particles within said bed is substantially uniform; and
      (iii) has a porosity less than thirty percent; and
      (iv) wherein the gaps and dead volume in the bed are substantially less than are the gaps and dead volume in a comparable bed formed from the same type of particles, where the comparable bed is formed by dry-packing the particles as a powder; and
   (b) driving the fluid through the bed in a radial direction, said radial driving being substantially uniform.

2. A process as recited in claim 1, additionally comprising the step of adjusting the temperature of the bed.

3. A process as recited in claim 2, wherein said temperature adjusting is programmable to adjust the temperature of the bed as a function of at least one selected variable.

4. A process as recited in claim 1, wherein said driving step drives the flow of a liquid.

5. A process as recited in claim 1, wherein said driving step drives the flow of a gas.

6. A process as recited in claim 1, wherein said driving step drives the flow of a supercritical fluid.

7. A process comprised of repeating the steps of the process of claim 1 with the same fluid sequentially at least once in each of at least two different beds, each bed being as described in said introducing step of claim 1.

\* \* \* \* \*